United States Patent [19]

Nakano et al.

[11] Patent Number: 5,397,536
[45] Date of Patent: Mar. 14, 1995

[54] SILANE GAS DETECTING TAPE

[75] Inventors: Nobuo Nakano; Akihiro Yamamoto, both of Tokyo, Japan

[73] Assignee: Riken Keiko Co., Ltd., Japan

[21] Appl. No.: 162,881

[22] Filed: Dec. 8, 1993

[30] Foreign Application Priority Data

Dec. 18, 1992 [JP] Japan ................................ 4-355512

[51] Int. Cl.$^6$ ............................................ G01N 31/22
[52] U.S. Cl. ........................................ 422/56; 422/86; 422/87; 422/88; 436/68; 436/73; 436/100; 436/104; 436/169
[58] Field of Search ..................... 422/56, 87, 86, 88; 436/73, 104, 169, 68, 100

[56] References Cited

U.S. PATENT DOCUMENTS

| | | | |
|---|---|---|---|
| 3,904,373 | 9/1975 | Harper | 422/57 |
| 4,420,567 | 12/1983 | McMahon et al. | 436/103 |
| 5,250,260 | 10/1993 | Nakano et al. | 422/56 |

FOREIGN PATENT DOCUMENTS 2-275352  9/1990  Japan .

*Primary Examiner*—Robert J. Warden
*Assistant Examiner*—N. Bhat
*Attorney, Agent, or Firm*—Pollock, Vande Sande & Priddy

[57] ABSTRACT

A porous cellulose tape impregnated with powdered silica or other gas adsorbent carries a coloring reagent of silver perchlorate or silver para-toluenesulfonate and a light-resistance enhancer of para-toluenesulfonic acid which are dissolved in glycol. When the tape is exposed to a sample gas, the silane contained in it dissolves in the glycol. The resulting reduction of the silver perchlorate or silver para-toluenesulfonate forms a colloid of silver as a trace of their reaction. The concentration of silane, which is proportional to the colloid of silver formed, can be determined by measuring the optical concentration of the reaction trace. The absence of strong acid detrimental to cellulose assures the determination of silane concentration with a high degree of sensitivity, without impairing the mechanical strength in the cellulose tape.

12 Claims, 5 Drawing Sheets

SILANE GAS DETECTING TAPE

BACKGROUND OF THE INVENTION

This invention relates to a detecting tape suited for optically detecting the presence of silane gas, which is one of gaseous hydrides, by examining a trace formed the reaction of silane gas with a coloring reagent placed on a cellulose tape.

The semi-conductor industry uses highly toxic gaseous hydrides such as phosphine ($PH_3$), silane gas ($SiH_4$), arsine ($AsH_3$) and diborane ($B_2H_6$). For the detection of their trace leakage, various types of gas detectors are employed. Coloring reagents bringing about optical changes on reaction with other substances are commonly preferred to electrochemical and semi-conductor gas sensors that do not have high enough sensitivity. By an integral effect, methods using a coloring reagent can produce a trace of reaction even with a target gas of low concentration if the sample size is increased. Checking the formed trace with an optical concentration meter provides a foolproof detection of gas leakage.

Silver nitrate is popularly used as a coloring reagent for this purpose. A hydride detecting tape consisting of a gas-permeable cellulose tape carrying silver nitrate thereon that forms a colloid of silver as a trace of reaction when coming in contact with a gaseous hydride for subsequent optical examination.

However, the hydride detecting tapes carrying silver nitrate must be kept in light-tight places because sliver nitrate has an extremely high light sensitivity. Even when such storage precaution is taken, silver nitrate becomes brown in as short a time as approximately 24 hours. A nitride detecting tape proposed in Japanese Provisional Patent Publication No. 99753 of 1983 has an improved light resistance. The light resistance is improved by minimizing the formation of silver colloid on exposure to light by adding a strong acid, such as nitric acid, to a cellulose tape impregnated with silver nitrate and a moisture absorbent. When kept in light-tight containers, this nitride detecting tape remains undiscolored for about half a year. However, nitric acid added for the improvement of light resistance deteriorates the reagent-carrying cellulose tape, with a resultant sharp decrease in its mechanical strength. This reduction in strength can lead to serious problems in automatic measuring apparatus incorporating gas sampling and optical concentration detecting devices. To achieve automatic measurement, a portion of the unused part of the gas detecting tape is fed into the measuring area for exposure at given intervals. Therefore, the detecting tape set in the measuring apparatus is usually wrapped around a pay-off reel and a take-up reel, with a portion of the tape being adapted to pass through the measuring area. On completion of one sampling, the pay-off reel feeds a given length of the tape into the measuring area. However, the large tensile force working thereon occasionally breaks the tape entailing an interruption of measurement.

To solve these problems, the inventor proposed a detecting tape having an improved light resistance obtained without impairing the mechanical strength of the reagent-carrying tape by adding para-toluenesulfonic acid instead of nitric acid (Japanese Provisional Patent Publication No. 275352 of 1990). Remaining undiscolored and losing no mechanical strength for long periods of time, this improved tape assures reliable detection on automatic measuring apparatus. Even this tape, however, suffers some discoloration when stored for long periods of time because highly light-sensitive silver nitrate is used as the coloring reagent. Therefore, it does not have high enough sensitivity to assure satisfactory detection of silane gas that does not exhibit as much coloring as other gaseous hydrides.

SUMMARY OF THE INVENTION

The object of this invention is to provide a silane gas detecting tape having a high light resistance and detection sensitivity without impairing the mechanical strength of the reagent carrier.

The silane detecting tape according to this invention consists of a porous carrier tape impregnated with a gas adsorbent carrying silver perchlorate, para-toluene-sulfonic acid and glycol as a coloring reagent, light-sensitivity enhancer and solvent, respectively. The low light sensitivity of silver perchlorate and the enhancement of light resistance by para-toluenesulfonic acid, in combination, bring about an extremely high light resistance without impairing the mechanical strength of the tape. Also, glycol increases the light sensitivity of the tape to such an extent as to assure the practically accurate detection of silane gas that does not exhibit as much coloring as other gaseous hydrides.

DETAILED DESCRIPTION OF THE INVENTION

Reagent-carrying cellulose tapes are made by slitting a gas-permeable sheet of plant fibers bleached to the maximum extent of whiteness and impregnated with a gas adsorbent, such as silicic acid ($H_2SiO_3$), magnesium oxide (MgO) and aluminum oxide ($Al_2O_3$).

The gas adsorbent impregnated in the cellulose tape carries gases, liquids and dissolved substances. Thus, the gas adsorbent always holds moisture necessary for the reaction between a gaseous hydrate and a coloring reagent and adsorbs silane gas from a collected sample for reaction with silver perchlorate impregnated in the tape.

The tape is then impregnated with 0.5 to 4.0 grams of silver perchlorate, 0.3 to 3 grams of para-toluenesulfonic acid and about 22.1 grams of ethylene glycol, each per square meter.

This impregnation is accomplished by dipping the cellulose tapes in a solution prepared by dissolving 0.75 to 6.0 w/v % of silver perchlorate, 0.5 to 4.5 w/v % of para-toluenesulfonic acid and 15 v/v % of glycol in an organic solvent such as methanol, lifting the tapes out of the solution, and allowing the organic solvent to evaporate at room temperature. Then, silver perchlorate, para-toluenesulfonic acid and ethylene glycol are impregnated in the tapes. By applying this process once or several times, depending on the concentration of the reagents in the solution, the tapes impregnated with the desired concentration of the reagents are obtained. The tapes thus prepared are impregnated with silver perchlorate and para-toluenesulfonic acid dissolved in ethylene glycol.

Figure 1:
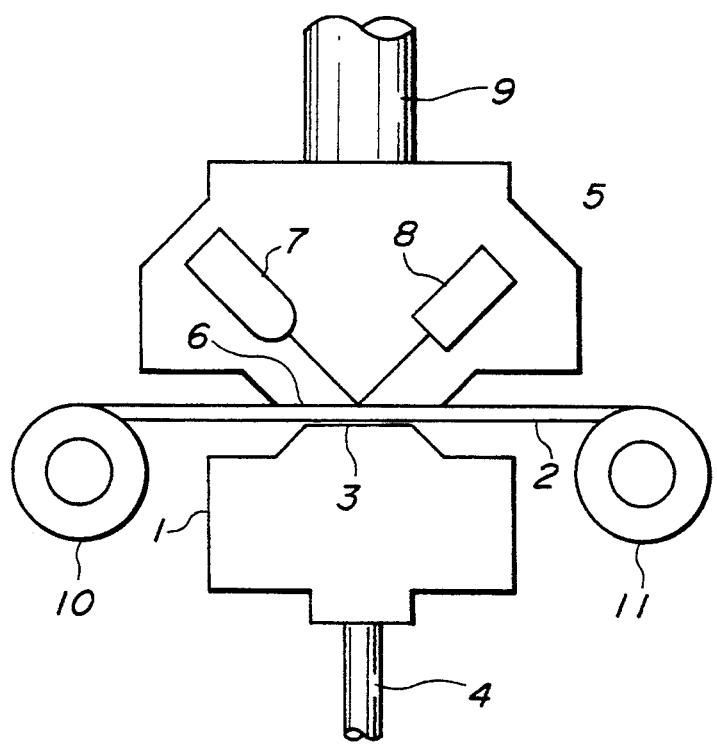
FIG. 1 illustrates the principle of a gas detector using a silane gas detecting tape according to this invention.

FIG. 1 shows an example of apparatus for determining the concentration of silane gas using a silane gas detecting tape according to this invention. Reference numeral 1 designates a gas suction segment disposed in the travel path of a tape 2. A through-hole 3 with a diameter of approximately 1 cm is provided in a surface of the gas suction segment that faces the tape 2 so that a negative pressure supplied through a pipe 4 through a suction pump (not shown) works thereon.

Reference numeral 5 designates a measuring head disposed opposite the through-hole 3 in the gas suction segment 1 and on the other side of the tape 2. The measuring head 5 consists of a light-tight container having a through-hole opposite the one in the suction segment 1, with a light transmitter 7 and a light receiver 8 disposed inside in such a positional relationship as to permit the detection of a trace of reaction formed on the tape 2 and a sample gas intake 9 provided at the top end thereof.

When suction is applied through the pipe 4 from the suction pump not shown after setting the silane gas detecting tape over the reels 10 and 11, a sample gas consisting of air containing silane gas enters the measuring head 5 through the intake 9. After passing through the through-hole 6, fine pores in the detecting tape 2, and through-hole 3, the sample gas is discharged into the atmosphere. When the sample gas passes over the detecting tape 2, the silane gas contained therein reacts with the silver perchlorate on the tape 2, entailing the precipitation of a silver colloid proportional to the concentration of silane gas on the surface of the tape.

When a given length of sampling time, such as 60 seconds, is over, application of the suction is stopped to proceed to the next step of determining the concentration of silane gas from the optical analysis of the reaction trace. The absorption of the light from the light transmitter 7 is proportional to the optical concentration of the reaction trace formed on the surface of the tape. Therefore, the concentration or integrated amount of silane gas in the sample gas can be determined by determining the difference between the derived optical concentration and the base figure established with the background of the tape prior to the start of detection.

On completion of one cycle, the take-up reel 10 is actuated to pull out a given length of the unused tape from the pay-off reel 11 into the measuring area.

Figure 2:
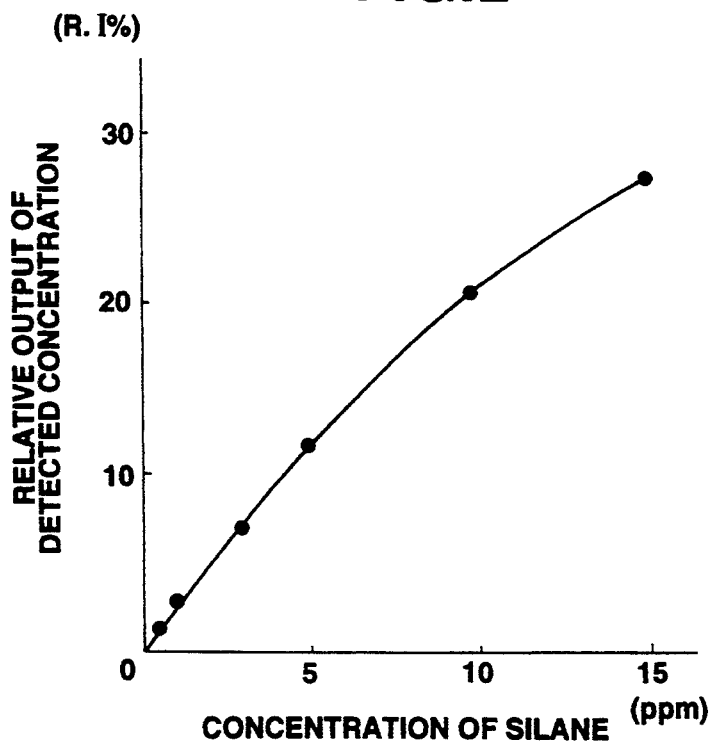
FIG. 2 graphically shows the relation ship between the concentration of silane gas and the relative output of detected silane gas concentration obtained by use of the first preferred embodiment of this invention.

FIG. 2 graphically shows the detection outputs obtained for varying concentrations of silane gas with the use of silane gas detecting tapes of this invention. Obviously, silane gas of the order of only a few ppm's can be detected with high enough accuracy.

Figure 3:
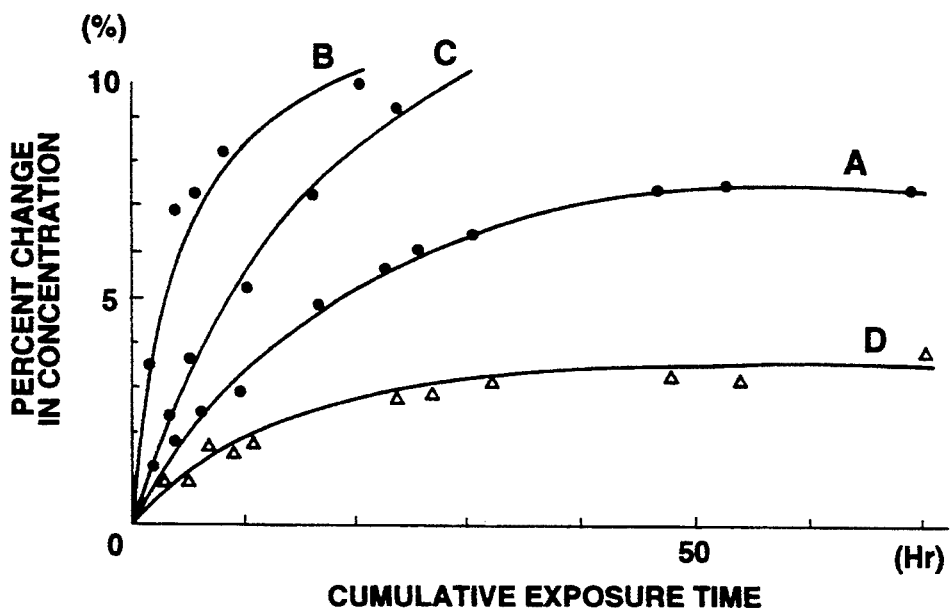
FIG. 3 graphically compares the relationships between the exposure time and the concentration change for the first preferred embodiment of this invention and conventional hydride detecting tapes.

The data shown in FIG. 3 was obtained by measuring the changes in the optical concentration of detecting tapes exposed to a light close to the natural light (with an illuminance of approximately 1500 lux) by placing them 20 cm under a 20-watt fluorescent lamp. With the optical concentrations of an unexposed silane gas detecting tape before exposure to the above light and after exposure over a given length of time defined as $D_O$ and $D_t$, respectively, the difference $(D_t - D_O)$ and the ratio $(D_t - D_O/D_O)$ were determined.

As is obvious from FIG. 3, the silane gas detecting tape of this invention (A) exhibits much less concentration changes with respect to exposure time than a conventional tape (B) prepared by impregnating a coloring reagent of silver nitrate and a light resistance enhancer of nitric acid and another conventional tape (C) prepared by using para-toluenesulfonic acid, instead of nitric acid, for the improvement of mechanical strength. The concentration changes of the tape of this invention are particularly small in the initial stage (with an integrated exposure time of approximately 10 hours), ranging between approximately one-third to a half those exhibited by the conventional tapes.

In ordinary storage conditions, detecting tapes are seldom exposed to light over such a long period of time as approximately 10 hours. Accordingly, the hydride detecting tapes according to this invention cause practically no optical concentration changes so long as they are stored under normal conditions. This feature is particularly advantageous in the detection of silane gas that does not exhibit as much coloring as other gaseous hydrides. Gas detecting tapes determine the presence of gases by determining the difference between pre-exposure and post-exposure optical concentrations, as described before. Therefore, tapes having lower pre-exposure optical concentrations are capable of detecting gases of lower concentrations.

When examined on a tension tester, a silane gas detecting tape of this invention proved to have a tensile strength of 0.55 kg/mm$^2$, as compared with 0.4 kg/mm$^2$ or approximately 70% of the above value, exhibited by a conventional hydride detecting tape prepared by impregnating a light resistance enhancer of nitric acid. The level of strength exhibited by the tape of this invention is high enough to assure a reliable detection on automatic measuring apparatus.

EXAMPLES

Cellulose tapes impregnated with a gas adsorbent was dipped in solutions prepared by dissolving 0.75 to 4 w/v % of silver perchlorate, 0.5 to 4.5 w/v % of para-toluenesulfonic acid and 15 v/v % of ethylene glycol in methanol. Then, the tapes were lifted out of the solution and the methanol impregnated in the tapes was vaporized at room temperature.

The obtained tapes carried 0.5 to 4 grams of silver perchlorate, 0.3 to 3.0 grams of para-toluenesulfonic acid and 22.1 grams of ethylene glycol per square meter.

Figure 4:
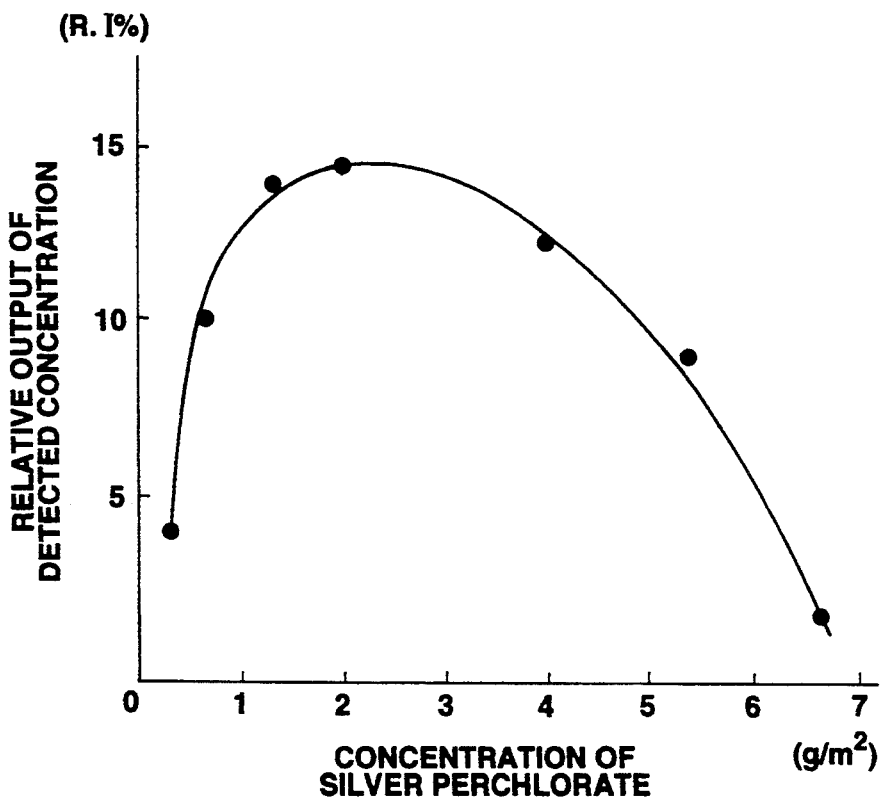
FIG. 4 graphically shows the relationship between the concentration of silver perchlorate and the relative output of detected silane gas concentration.

The silver perchlorate concentration of not less than 0.5 gram per square meter proved to provide a practically high enough detection sensitivity, as shown in FIG. 4. Entailing lowered detection sensitivity and increased coloring reagent consumption, the silver perchlorate concentration in excess of 4 grams per square meter proved uneconomical, although detection was still possible.

Figure 5:
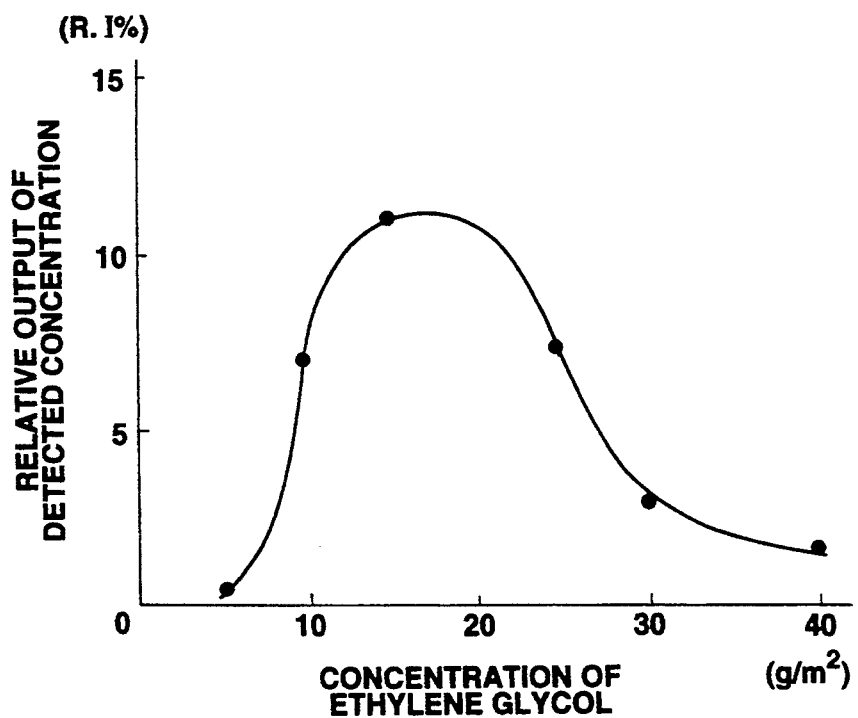
FIG. 5 graphically shows the relationship between the concentration of ethylene glycol and the relative output of detected silane gas concentration.
Figure 6:
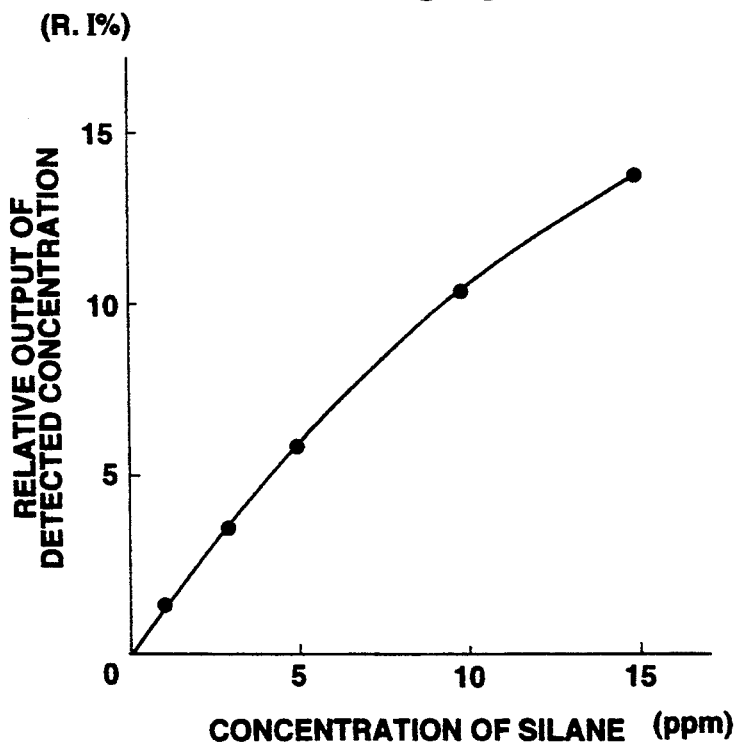
FIG. 6 graphically shows the relation ship between the concentration of silane gas and the relative output of detected silane gas concentration obtained by use of the second preferred embodiment of this invention.
Figure 7:
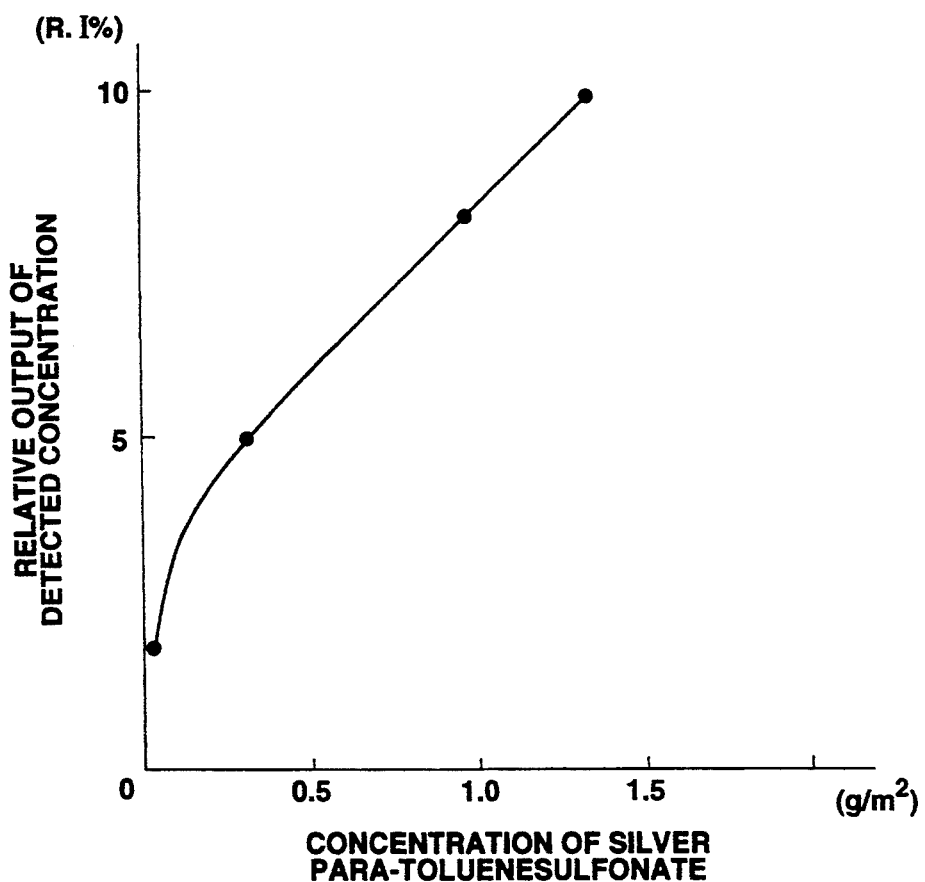
FIG. 7 graphically shows the relationship between the concentration of para-toluenesulfonic acid and the relative output of detected silane gas concentration.

The relationship between the quantity of ethylene glycol carried by the tapes and their detection sensitivity was examined without varying the concentration of silane gas. The tapes carrying small quantities of ethylene glycol exhibited very low detection sensitivities irrespective of the concentration of silver perchlorate added as a coloring agent, as shown in FIG. 5. Practically adequate sensitivities were obtained when the ethylene glycol concentration exceeded 15 grams per square meter. However, long exposure to the sample gas, which usually lasts for 60 seconds or occasionally as long as 20 minutes, vaporizes ethylene glycol from the surface of the tapes, with a resulting decrease in detection sensitivity. On the other hand, the ethylene glycol concentration in excess of 40 grams per square meter also lowers detection sensitivity by impairing the gas permeability of the tapes and preventing the contact between silane gas and silver perchlorate.

All things considered, the practically optimum ethylene glycol concentration proved to fall within the range of 15 to 40 grams per square meter. While the ethylene glycol concentration of 22.1 grams per square meter proved to provide the highest detection sensitivity, that of 40 grams per square meter proved to assure a long stable sensitivity.

Other tapes were prepared by using trimethylene glycol, which is a dihydric alcohol having properties similar to those of ethylene glycol, as the solvent. To be specific, cellulose tapes impregnated with a gas adsorbent was dipped in solutions prepared by dissolving 0.75 to 4 w/v % of silver perchlorate, 0.5 to 4.5 w/v % of para-toluenesulfonic acid and 15 v/v % of trimethylene glycol in methanol. Then, the tapes were lifted out of the solution and the methanol impregnated in the tapes was vaporized at room temperature.

The obtained tapes carried 0.5 to 4 grams of silver perchlorate, 0.3 to 3.0 grams of para-toluenesulfonic acid and 20.8 grams of trimethylene glycol per square meter.

The obtained tapes proved to have identical light resistance, mechanical strength and sensitivity to silane gas to those of the tapes prepared with the use of ethylene glycol. While the trimethylene glycol concentration of 20.8 gram per square meter proved to provide the highest detection sensitivity, that of 37.5 grams per square meter proved to assure a long stable sensitivity.

Different tapes were prepared by a similar method, except that silver para-toluenesulfonate was used instead of silver perchlorate. Cellulose tapes impregnated with a gas adsorbent was dipped in solutions prepared by dissolving not less than 0.5 w/v % of silver para-toluene-sulfonate (which saturates at approximately 4 w/v % at room temperature because of this extremely low solubility), 0.5 to 4.5 w/v % of para-toluenesulfonic acid and 15 v/v % of ethylene glycol in methanol. Then, the tapes were lifted out of the solution and the methanol impregnated in the tapes was vaporized at room temperature.

The obtained tapes carried 0.3 to 1.4 grams of silver para-toluenesulfonate, 0.3 to 3.0 grams of para-toluene-sulfonic acid and 22.1 grams of ethylene glycol per square meter.

Para-toluenesulfonate used as the coloring agent with the tapes of this type has a lower light sensitivity than that of silver perchlorate. Therefore, these tapes suffer less decrease in detection sensitivity during long storage, as indicated by curve D in FIG. 3 and assure the detection of small quantities of silane gas with a high degree of sensitivity and reliability.

An investigation on the influence of the concentration of silver para-toluenesulfonate on detection sensitivity revealed that practically adequate sensitivities were obtainable when the concentration of silver para-toluene-sulfonate exceeded 0.3 gram per square meter. Not more than approximately 1.4 grams per square meter of silver para-toluenesulfonate is applicable in one dip because of its extremely low solubility. The use of more silver para-toluenesulfonate results in an uneconomical increase in the consumption of the coloring reagent.

Figure 8:
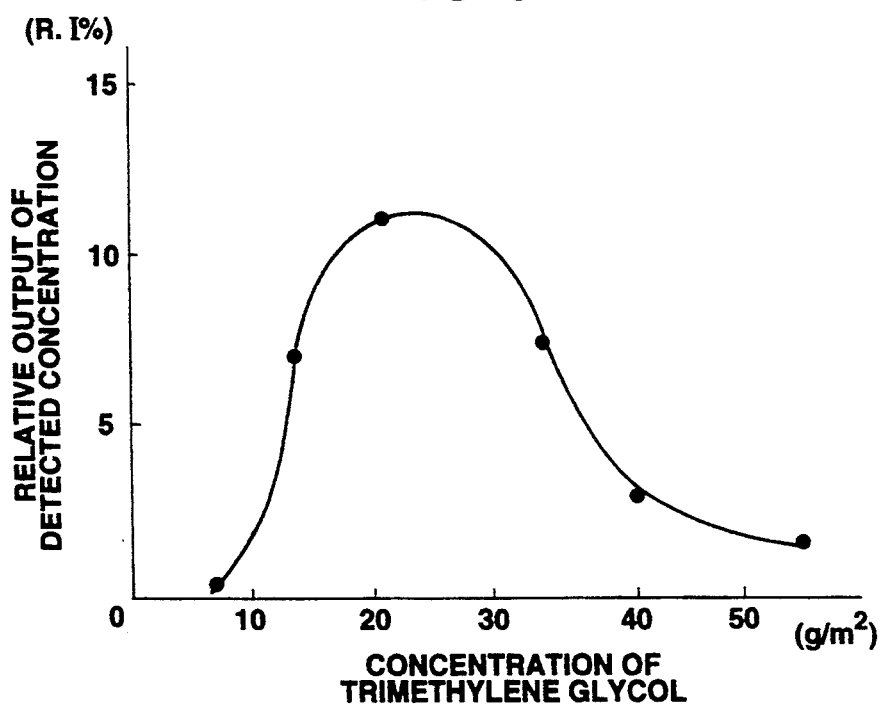
FIG. 8 graphically shows the relationship between the concentration of glycol and the relative output of detected silane gas concentration obtained by using para-toluenesulfonic acid as a coloring reagent.

The effect of the concentration of ethylene glycol and trimethylene glycol proved similar to that of silver perchlorate, as shown in FIG. 8. When silver para-toluenesulfonate is used as the coloring reagent, therefore, practically satisfactory silane gas detection tapes are obtained by applying 15 to 40 grams per square meter of ethylene glycol and 14 to 37.5 grams per square meter of trimethylene glycol, as in the case of silver nitrate. The quantitative difference between ethylene glycol and methylene glycol is due to the difference in their specific weight.

Figure 9:
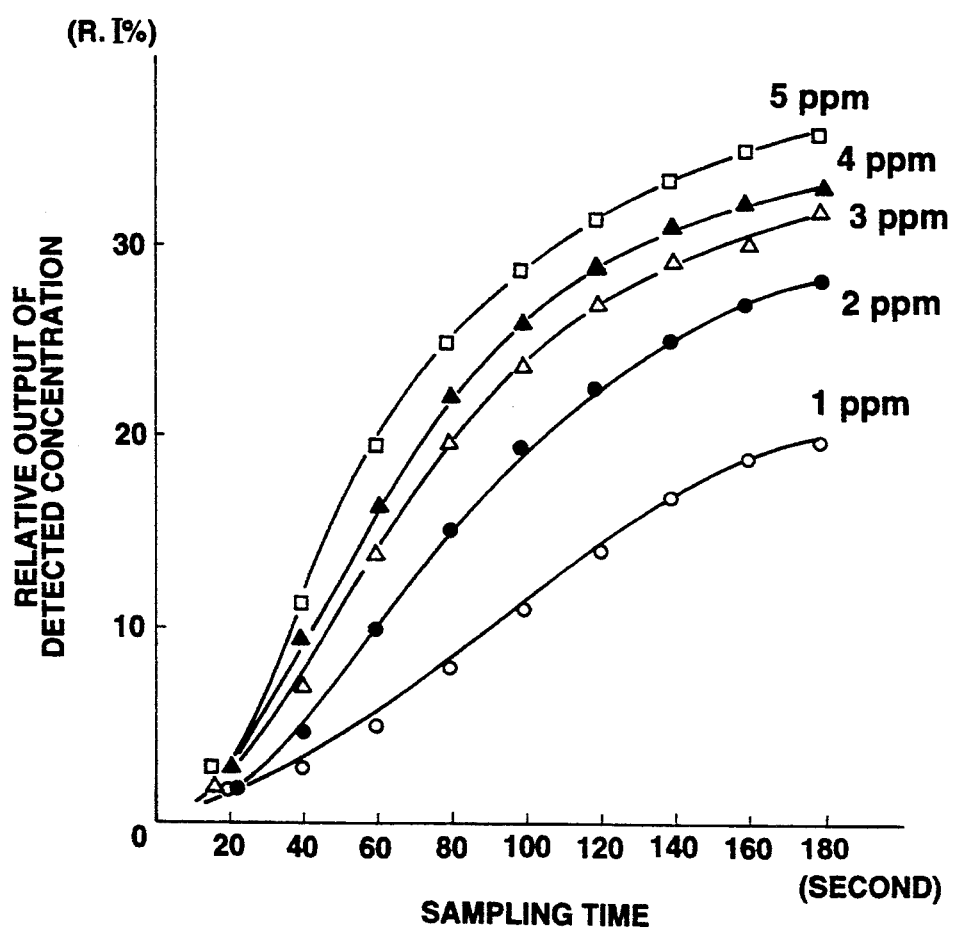
FIG. 9 graphically shows the relationship between the sampling time and the relative output of detected silane gas concentration obtained by using a silane gas detecting tape according to this invention.

The relationship between the sampling time and the relative output of detected silane gas concentration tapes was investigated by using the concentration of silane gas as a parameter. Detection output increased with increasing sampling time, as shown in FIG. 9. When sampling time was prolonged, the tapes exhibited high enough detection sensitivities to the sample gases of lower saline concentrations, without causing the spattering of glycol or other coloring agents.

Although individual reagents used in the above examples were dissolved in methanol or other lower alcohol, coloring reagents and light-resistance enhancers directly dissolved in glycol may be applied with a spray or other suitable apparatus.

What is claimed is:

1. A silane gas detection tape consisting of a gas-permeable cellulose tape impregnated with a gas adsorbent and carrying a coloring agent of silver perchlorate, a light-sensitivity enhancer of para-toluenesulfonic acid, and glycol wherein said glycol is selected from the group consisting of 15 to 40 grams of ethylene glycol per square meter of the tape, and 14 to 37.5 grams of trimethylene glycol per square meter of the tape.

2. A silane gas detection tape according to claim 1, which carries 0.5 to 4.0 grams of silver perchlorate and 15 to 40 grams of ethylene glycol per square meter of the tape.

3. A silane gas detection tape according to claim 1, which carries 0.5 to 4.0 grams of silver perchlorate and 14 to 37.5 grams of trimethylene glycol per square meter of the tape.

4. A silane gas detection tape according to claims 1 which carries 0.3 to 3.0 grams of paratoluenesulfonic acid per square meter of the tape.

5. A silane gas detection tape consisting of a gas-permeable cellulose tape impregnated with a gas adsorbent and carrying a coloring agent of silver para-toulene-sulfonate, sulfonate, a light-sensitivity enhancer of para-toluene-sulfonic acid, and glycol wherein said glycol is selected from the group consisting of 15 to 40 grams of ethylene glycol per square meter of the tape, and 14 to 37.5 grams of trimethylene glycol per square meter of the tape.

6. A silane gas detection tape according to claim 5, which carries at least 0.3 gram of silver para-toluenesulfonate and 15 to 40 grams of ethylene glycol per square meter of the tape.

7. A silane gas detection tape according to claim 5, which carries at least 0.3 gram of silver para-toluenesulfonate and 14 to 37.5 grams of trimethylene glycol per square meter of the tape.

8. A silane gas detection tape according to claim 5 which carries 0.3 to 3.0 grams of para-toluene-sulfonic acid per square meter of the tape.

9. A silane gas detection tape according to claim 2, which carries 0.3 to 3.0 grams of para-toluenesulfonic acid per square meter of the tape.

10. A silane gas detection tape according to claim 3, which carries 0.3 to 3.0 grams of para-toluenesulfonic acid per square meter of the tape.

11. A silane gas detection tape according to claim 6, which carried 0.3 to 3.0 grams of para-toluenesulfonic acid per square meter of the tape.

12. A silane gas detection tape according to claim 7, which carried 0.3 to 3.0 grams of para-toluenesulfonic acid per square meter of the tape.

* * * * *